United States Patent [19]

Laine et al.

[11] Patent Number: 4,612,383

[45] Date of Patent: Sep. 16, 1986

[54] METHOD OF PRODUCING POLYSILAZANES

[75] Inventors: Richard M. Laine, Palo Alto; Yigal Blum, Menlo Park, both of Calif.

[73] Assignee: S R I International, Menlo Park, Calif.

[21] Appl. No.: 727,415

[22] Filed: Apr. 26, 1985

[51] Int. Cl.⁴ ............................................... C07F 7/10
[52] U.S. Cl. ...................................... 556/412; 528/15
[58] Field of Search ........................... 556/412; 528/15

[56] References Cited

U.S. PATENT DOCUMENTS

| | | | |
|---|---|---|---|
| 2,579,418 | 12/1951 | Cheronis | 556/412 X |
| 3,007,886 | 11/1961 | Parker | 556/412 |
| 3,393,218 | 7/1968 | Van Wazer et al. | 556/42 |
| 4,482,669 | 11/1984 | Seyferth et al. | 556/412 X |

Primary Examiner—Paul F. Shaver
Attorney, Agent, or Firm—Edward B. Gregg; Urban H. Faubion; John Y. Chen

[57] ABSTRACT

Method of producing polysilazanes from precursors having Si-H, Si-N or Si-Si bonds in the presence of a catalyst effective to activate such bonds. The catalyst may be a metal complex, e.g. a carbonyl cluster, which is soluble in an organic solvent and is homogeneous or it may be a heterogeneous catalyst. Higher polymers, and/or less crosslinking and oligomer formation, and/or greater control over the product and/or faster reactions and/or greater yields result. The polymers are soluble in common organic solvents and/or are solids which can be shaped. The products can be pyrolyzed to silicon nitride or used without pyrolysis.

13 Claims, No Drawings

METHOD OF PRODUCING POLYSILAZANES

This invention was funded in part by the Office of Naval Research under Contract No. N00014-84-C-0392.

This invention relates to the preparation of polysilazanes, i.e. polymers having the repeating unit

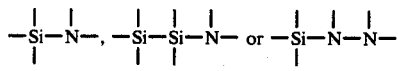

Other elements, for example carbon or oxygen, may be also present in the repeating unit.

Polysilazanes are useful among other things for the preparation of silicon nitride, $Si_3N_4$, by pyrolysis. Silicon nitride is a hard material and is useful in forming fibers for reinforcement of composite materials. See, for example, (a) Department of Defense Proceedings. Fourth Metal Matrix Composites Technical Conference, May 19-21, 1981, prepared for DOD Metal Matrix Composites Information Analysis Center and (b) J. J. Brennan, "Program to Study Sic Fiber-Reinforced Glass Matrix Composites, Annual Report to Dept. of Navy (Nov. 1980), Contract No. N00014-78-C-0503.

A number of researchers have developed methods of forming polysilazanes, among them Redl and Rochow, who, in Angew. Chemie. (1964) 76, 650 discuss the preparation of polysilazanes by reaction (1)

$$[(CH_3)_2SiNH]_3 + NH_3 \rightarrow -[(CH_3)_2SiNH]_n- \quad (1)$$

Brewer and Haber, J. Am. Chem. Soc. (1948) 70, 3888 and Osthoff and Kantor, Inorg. Syn. (1957) 5, 61 teach the reaction (2)

$$(CH_3)_2SiCl_2 + NH_3 \rightarrow [(CH_3)_2SiNH]_n + HCl \quad (2)$$

More recent work is described by Markle and others in R. A. Markle, I. Sekercioglu, D. L. Hill, R. R. Wills, and R. G. Sinclair, "Preparation of $Si_xN_yC_z$ Fibers by the Controlled Pyrolysis of Novel Organosilicon Polymeric Precursors", Final Report to NASA, Marshall Flight Center, Alabama, (1981), Contract No. NAS8-33223.

Zoeckler and Laine in J. Org. Chem. (1983) 48, 2539-2541 describe the catalytic activation of the Si—N bond and in particular the ring opening of octamethyl tetrasilazane, $$[(CH_3)_2SiNH]_4$$

and polymerization of the ring-opened intermediate. Chain termination is effected by means of [(CH₃)₃Si]₂NH giving rise to polymers (CH₃)₃Si—[N-HSi(CH₃)₂]ₙ—NHSi(CH₃)₃ where n=1-6 or 1-12 depending upon the ratio of the chain terminator to the cyclic silazane. The catalyst used was $Ru_3(CO)_{12}$. Other publications are as follows: W. Fink, Helv. Chem. Acta., 49, 1408 (1966); Belgian Pat. No. 665774 (1965); Netherlands Pat. No. 6,507,996 (1965); D. Y. Zhinkis et al., Rus. Chem. Rev., 49, 2814 (1980) and references 51-58; K. A. Andrianov et al., Dok Akad. Nauk. SSSR, 227, 352 (1976); Dok Akad. Nauk. SSSR, 223, 347 (1975); L. H. Sommer et al., JACS 91, 7061 (1969); L. H. Sommer, J. Org. Chem. (1967) 32 2470; L. H. Sommer et al., JACS 89, 5797 (1967).

The methods described in the literature cited above and elsewhere have resulted in one or more of the following disadvantages: low yields of polysilazanes coincident with a high yield of cyclomers, lack of control over product selectivity or quality, etc. Often the product is volatile and is therefore difficult to pyrolyze, or if it is solid, it is an intractable material which cannot be readily shaped, if indeed it can be shaped at all. The product is likely to be contaminated with halogen, especially chloride and it may be extensively cross linked and insoluble. In addition, the high ratio of Si to N in the polymers leads to formation of silicon along with $Si_3N_4$ on pyrolysis.

It is an object of the present invention to provide improved methods of preparing polysilazanes.

It is a particular object of the present invention to provide a method of preparing polysilazanes which results in high yields of linear polymers which are devoid of or are substantially devoid of cross links except where desired.

The above and other objects of the invention will be apparent from the ensuing description and the appended claims.

In accordance with one embodiment of the present invention a silane $R_2SiH_2$ is reacted with ammonia, hydrazine or a primary amine in the presence of a suitable catalyst to effect the reaction

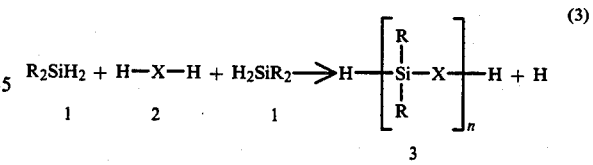

In the above, R is preferably a hydrocarbon group, e.g. alkyl (e.g. methyl, ethyl, etc.), aryl (e.g. phenyl), cycloaliphatic (e.g. cyclohexyl) or aralkyl (e.g. benzyl) and the R's may be the same or different. R may also be an amino group, an alkoxy group, an ether group, an ester group, a silyl group, hydrogen, an alkenyl group, etc. X is

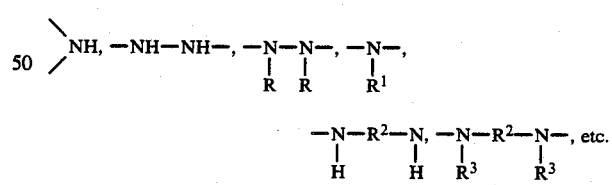

where $R^1$, $R^2$ and $R^3$ are defined as is R above, $R^2$ being, however, a bivalent group.

Instead of using a silane 1, a low molecular weight silazane may be used such as 4 in reaction (4)

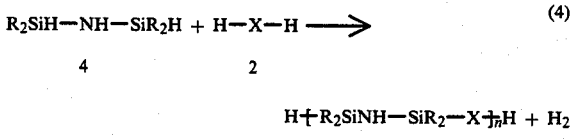

In this embodiment of the invention the silazane 4 may be an oligomer 4a

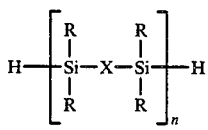

4a where n is a small number, e.g. 3 or 4 and R is as defined above or is H.

In another embodiment of the invention a cyclic polysilazane is caused to undergo cleaveage of an Si—N bond thus opening the ring

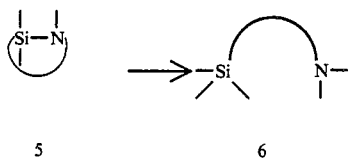

and the open chain intermediate 6 undergoes polymerization. This is the method of Zoeckler and Laine, supra, but is modified and greatly improved as described below in Example 7. The resulting polymer may be variously treated. One method of treatment is with a capping agent. Depending upon the capping agent, the intermediate 6 and the ratio of the two, polymers of 6 capped by the capping agent will result. The reaction is carried out under nitrogen or hydrogen, preferably hydrogen.

Another method is to treat the intermediate with molecular hydrogen, thus in effect capping the polymer with hydrogen.

Another method is to cleave an Si—Si bond as follows:

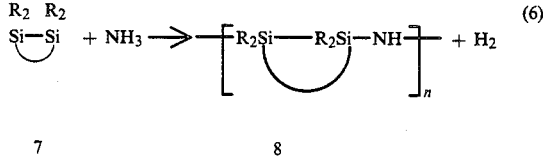

The R's, which may be the same or different, are as defined above. Instead of $NH_3$, hydrazine, primary amines, etc. may be used. I.e., the reactant may be H—X—H as defined above.

Catalysts suitable for carrying out these reactions are metal complexes such as those in Table I which are homogeneous catalysts that dissolve in the reactants or in a solvent used to dissolve the reactants. Heterogeneous catalysts such as those in Table II may also be used. In general catalysts that activate the Si—H bond or the Si—N bond may be used.

The reactions are carried out in solution, the solvent being the reactants themselves or an added solvent. Suitable solvents are set forth in Table III. Temperature may range from 0° to 250°, preferably 60° to 150°.

TABLE 1, HOMOGENEOUS CATALYSTS $H_4Ru_4(CO)_{12}$, $Ru_3(CO)_{12}$, $Fe_3(CO)_{12}$, $Rh_6(CO)_{16}$, $Co_2(CO)_8(Ph_3P)_2Rh(CO)H$, $H_2PtCl_6$, nickel cyclooctadiene, $Os_3(CO)_{12}$, $Ir_4(CO)_{12}$, $(Ph_3P)_2Ir(CO)H$, $Pd(OAc)_2$, $Cp_2TiCl_2$, $(Ph_3P)_3RhCl$, $H_2Os_3(CO)_{10}$, $Pd(Ph_3P)_4$, $Fe_3(CO)_{12}/Ru_3(CO)_{12}$ mixtures.

TABLE 2, HETEROGENEOUS CATALYSTS

Pt/C, $Pt/BaSO_4$, Cr, Pd/C, Co/C, Pt black, Co black, Pd black, $Ir/Al_2O_3$, $Pt/SiO_2$, $Rh/TiO_2$, $Rh/La_2O_3$, Pd/Ag alloy, $LaNi_5$, $PtO_2$.

TABLE 3, SOLVENTS

Ethers such as $Et_2O$, $CH_3O—CH_2CH_2OCH_3$

Halocarbons such as $CHCl_3$, $CH_2Cl_2$, $HClCF_2$, $ClCH_2CH_2Cl$

Aromatics such as PhH, $PhCH_3$, $Ph—OCH_3$.

The following specific examples will serve to illustrate the practice and advantages of the invention.

EXAMPLE 1

To 3.9 mmol (5 ml) of diethylsilane ($Et_2SiH_2$) are added 25 μmol of $Ru_3(CO)_{12}$ and the solution is heated at 135° C. under 60 psi of $NH_3$. The reaction is very fast producing oligomers, polymers and $H_2$. The $H_2$ pressure rises to 110 psi and is released every 0.5 hours. The reactor is again charged to 60 psi with $NH_3$. After 1 h all of the $Et_2SiH_2$ reacts and no further release of $H_2$ occurs.

EXAMPLE 2

To 30 mmol of tetramethyldisilazane (TMDS) are added 25 μmol of $Ru_3(CO)_{12}$ and the solution is heated at 135° C. under 80 psi of $NH_3$. TMDS disappears totally after 20 h and polymerization continues for 28 h. The polymeric residue (heavy oil) is 2.44 gm (yield 61 wt%) after distillation at 180°/0.3 mm Hg with a wt average MW of 764. The major polymeric series is the linear $HSiMe_2[NHSiMe_2]_xNHSiMe_2H$. Also smaller branched chain polymers appear.

EXAMPLE 3

To 20 mmol of TMDS are added 25 μmol of $Ru_3(CO)_{12}$ and the solution is heated at 135° C. under 100 psi of $NH_3$. The conversion of TMDS is 94% after 1 h. 0.1 g of hydrazine are added and the solution is heated again for 3 hours. The GC shows that most of volatile products disappear. The high polymeric residue is 68 wt% after distillation at 180°/0.3 mm Hg. Similar results are achieved by using 200 mg of 5% Pt/C (activated under $H_2$) using identical conditions. The average molecular weight is 1200.

EXAMPLE 4

To 75 mmol of TMDS are added 25 μmol of $Ru_3(CO)_{12}$ and the solution is heated at 135° C. under 60 psi of ammonia. The hydrogen pressure produced in the reaction is released every 1 hour and the reactor is charged again with 60 psi of $NH_3$. TMDS disappears after 5 h. The initial turnover frequency (TF) for TMDS disappearance is 260. The net total turnover number of Si-N bond production is close to 4,480 after 8 hours.

EXAMPLE 5

To 20 mmol of tetramethyldisilazane (TMDS) and 20 mmol anhydrous hydrazine ($NH_2NH_2$) are added 25 μmol of $Ru_3(CO)_{12}$ and the solution is heated at 135° C. under nitrogen. All the TMDS disappears after 3 hours and $H_2$ pressure is obtained (TF=528). The yield of the polymeric residue after distillation of the volatile products is 75 wt percent. The average molecular weight is 968.

EXAMPLE 6

To 1.8 gr polydimethylsilylhydrazine [Me$_2$SiNHNH]$_x$ prepared as follows:

$$(CH_3)_2SiCl_2 + NH_2NH_2 \rightarrow [(CH_3)_2SiNHNH]_n + HCl \qquad (7)$$

(average MW 1130) dissolved in 5 ml of toluene are added 25 μmol of Ru$_3$(CO)$_{12}$ and the solution is heated at 135° C. under hydrogen. The clear solution turns cloudy and viscous (at room temperature). 1.3 g of a soft solid product is obtained after distillation of the volatile products and solvent at 180°/0.3 mm Hg. The solid has a wt average MW 1220 and starts to soften at 60° C. The same treatment for the starting material in the absence of catalyst gives a slightly cloudy solution at room temperature (clear during heating). The wt average MW decreases to 612. The product is a solid after distillation and does not soften up to 250° C.

EXAMPLE 7

Octamethyltetrasilazane

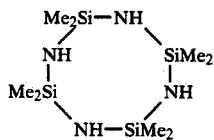

9 was reacted with [(CH$_3$)$_3$Si]$_2$NH, in the presence of various catalysts. The reaction conditions, catalysts and results are set forth in Table 4.

TABLE 4

| Run | Catalyst | Temp (°C.) | Time (h) | Conversion (%) | Decomposition |
|---|---|---|---|---|---|
| 1 | Ru$_3$(CO)$_{12}$ | 135 | 6 | 22 | s |
| 2 | Ru$_3$(CO)$_{12}$ | 180 | 15 | 80 | m |
| 3 | Ru$_3$(CO)$_{12}$/H$_2$ | 135 | 1 | 78 | — |
| 4 | Ru$_3$(CO)$_{12}$/H$_2$O | 135 | 3 | 33 | s |
| 5 | Ru$_3$(CO)$_{12}$/Fe(CO)$_5$ | 135 | 6 | 26 | s |
| 6 | Ru$_3$(CO)$_{12}$/Fe$_3$(CO)$_{12}$ | 135 | 3 | 80 | s |
| 7 | Fe$_3$(CO)$_{12}$ | 135 | — | — | — |
| 8 | Fe$_3$(CO)$_{12}$/H$_2$ | 135 | 3 | 80 | f |
| 9 | Os$_3$(CO)$_{12}$ | 135 | — | — | — |
| 10 | Os$_3$(CO)$_{12}$ | 180 | 20 | 78 | — |
| 11 | Os$_3$(CO)$_{12}$/H$_2$ | 135 | 6 | 73 | — |
| 12 | H$_2$Os$_3$(CO)$_{10}$ | 135 | 3 | 78 | — |
| 13 | Rh$_6$(CO)$_{16}$ | 135 | 20 | 55 | g |
| 14 | Rh$_6$(CO)$_{16}$/H$_2$ | 135 | 3 | 78 | g |
| 15 | Ir$_4$(CO)$_{12}$ | 135 | — | — | — |
| 16 | Ir$_4$(CO)$_{12}$ | 180 | 15 | 70 | m |
| 17 | Ir$_4$(CO)$_{12}$/H$_2$ | 135 | 3 | 76 | f |
| 18 | Pt/C$^f$ | 135 | 3 | 75 | — |
| 19 | PtO$_2$ | 180 | 15 | 25 | — |
| 20 | Pd/C | 135 | 3 | 78 | — |

Comments on Table 4 are as follows: The molar ratio of 9, the silazane [(CH$_3$)$_3$Si]$_2$NH and catalyst was 250:84:1. The reaction was carried out under hydrogen where indicated, as in Run No. 3, or water in Run No. 4, otherwise under nitrogen. The hydrogen was at 1 atmosphere pressure. The time figures indicate the shortest time in which there was no further conversion of 9. Butyl ether was used as an internal standard for glass chromatography analysis. In the decomposition column, "s" means slow, "m" means moderate and "f" means fast. In Run No. 4 the ratio of Ru$_3$(CO)$_{12}$ to H$_2$O was 1:22. In Run No. 18, 200 mg of 5% Pt/C were used and in Run No. 20, 150 mg of 5% Pd/C were used.

It will be seen that in the presence of hydrogen (Runs No. 3, 8, 11, 14 and 17) the reaction was much faster and gave significantly higher yields than in comparable runs with nitrogen. The mixed catalyst in Run No. 6 resulted in a fast reaction and a high yield even in the absence of hydrogen. In Run No. 12 a nitrogen atmosphere was used. The reaction rate and yield were comparable to Run No. 11 where a hydrogen atmosphere was used, perhaps because of the presence of hydrogen in the complex. In Runs Nos. 7, 9 and 15 no appreciable reaction occurred.

In addition to the silanes and silazanes mentioned above, the following may also be used:

Silanes R$_2$SiH—SiH$_3$; RSiH$_2$—SiHR$_2$; R$_2$SiH—SiHR$_2$; RSiH$_3$ where R=alkyl such as methyl or ethyl, aryl such as phenyl, etc.

Silazanes

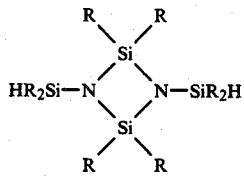

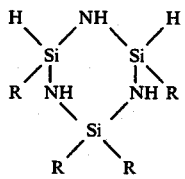

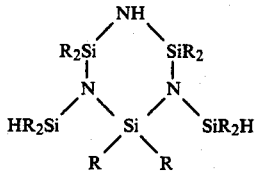

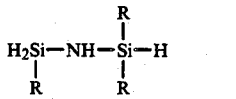

In the above formulas, R is as defined above.

It will, therefore be apparent that a new and useful method of producing polysilazanes has been provided.

We claim:

1. A method of preparing polysilazanes having the repeating structure I $$-Si-N- \qquad\qquad I$$

which comprises:

(a) providing a starting material having the structure II in its molecule $$-Si-A \qquad\qquad II$$

in which A is hydrogen, N< or

structure II being part of a linear structure or part of a cyclic structure (b) providing a catalyst which is effective to activate Si—H, Si—N and/or Si—Si bonds, and (c) reacting the starting material in the presence of such catalyst with (1) hydrogen where A is nitrogen and structure II is part of a cyclic silazane or (2) with H—X—H in other cases, X being selected from the group >NH, —NR, —NH—NH—,

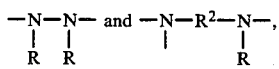

R being hydrogen or an organic group or a silyl group and $R^2$ being a bivalent organic group (d) thereby forming a polymer having the repeating unit

2. The method of claim 1 wherein R is hydrogen or a hydrocarbon group.

3. The method of claim 1 wherein the catalyst is a homogeneous catalyst.

4. The method of claim 3 wherein the catalyst is a metal complex.

5. The method of claim 4 wherein the catalyst is a metal carbonyl cluster.

6. The method of claim 1 wherein the catalyst is a heterogeneous catalyst.

7. The method of claim 1 wherein the reaction is carried out in an organic solvent at a temperature of about 60° to 150° C.

8. The method of claim 1 wherein the starting material is a cyclic silazane and it is reacted with hydrogen.

9. The method of claim 1 wherein the starting material is a linear silazane and it is reacted with H—X—H.

10. The method of claim 9 wherein H—X—H is ammonia.

11. The method of claim 9 wherein H—X—H is a primary amine.

12. The method of claim 9 wherein H—X—H is hydrazine or a substituted hydrazine.

13. The method of claim 1 wherein the starting material is a cyclic compound containing an Si—Si bond in the ring and it is reacted with H—X—H.

* * * * *